(12) United States Patent
Davies

(10) Patent No.: US 10,460,133 B2
(45) Date of Patent: *Oct. 29, 2019

(54) SYSTEMS AND METHODS FOR CORRECTION OF ON-STRIP CODING

(71) Applicant: Trividia Health, Inc., Fort Lauderdale, FL (US)

(72) Inventor: Stephen Davies, Coconut Creek, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,393

(22) Filed: Aug. 10, 2018

(65) Prior Publication Data

US 2019/0042806 A1 Feb. 7, 2019

Related U.S. Application Data

(60) Continuation of application No. 15/879,699, filed on Jan. 25, 2018, now Pat. No. 10,073,991, which is a division of application No. 15/455,385, filed on Mar. 10, 2017, now Pat. No. 9,911,013.

(60) Provisional application No. 62/306,927, filed on Mar. 11, 2016.

(51) Int. Cl.
*G06K 19/06* (2006.01)
*G06K 1/12* (2006.01)
*C12Q 1/00* (2006.01)
*G01N 33/66* (2006.01)
*G06K 19/067* (2006.01)

(52) U.S. Cl.
CPC ............ *G06K 1/121* (2013.01); *C12Q 1/006* (2013.01); *G01N 33/66* (2013.01); *G06K 19/067* (2013.01)

(58) Field of Classification Search
USPC .................................. 235/375, 462.01, 494
See application file for complete search history.

(56) References Cited

U.S. PATENT DOCUMENTS

| | | | |
|---|---|---|---|
| 5,366,609 A | 11/1994 | White et al. | |
| 5,820,826 A | 10/1998 | Moorman | |
| 6,168,957 B1 | 1/2001 | Matzinger et al. | |
| 6,377,894 B1 * | 4/2002 | Deweese | G06F 19/00 702/22 |

(Continued)

OTHER PUBLICATIONS

International Search Report for International Application No. PCT/US17/21808, dated May 26, 2017.

*Primary Examiner* — Tuyen K Vo
(74) *Attorney, Agent, or Firm* — Greenberg Traurig, LLP; David J. Dykeman; Roman Fayerberg

(57) ABSTRACT

Systems and methods of making a diagnostic test strip, the method including marking a machine-readable pattern onto the diagnostic test strip which contains information that allows a meter designed to work with the test strip to convert raw signal data from the diagnostic test strip into a meaningful concentration value for an analyte of interest. The method further includes printing the machine-readable pattern having a modified based code that is different from a base code of the diagnostic test strip being produced, wherein the modified based code is based on a strip geometry parameter, a chemistry parameter or both the strip geometry and chemistry parameters that are measured for the diagnostic test strip.

18 Claims, 11 Drawing Sheets

(56) References Cited

U.S. PATENT DOCUMENTS

| | | |
|---|---|---|
| 2003/0207454 A1 | 11/2003 | Eyster et al. |
| 2005/0279647 A1 | 12/2005 | Beaty |
| 2006/0144704 A1* | 7/2006 | Ghesquiere ............ C12Q 1/001 |
| | | 204/403.01 |
| 2006/0231418 A1 | 10/2006 | Harding et al. |
| 2007/0110615 A1 | 5/2007 | Neel et al. |
| 2007/0117171 A1 | 5/2007 | Wegner et al. |
| 2007/0273928 A1 | 11/2007 | Robinson et al. |
| 2007/0287182 A1 | 12/2007 | Morris et al. |
| 2008/0003709 A1 | 1/2008 | Wegner et al. |
| 2008/0020452 A1 | 1/2008 | Popovich et al. |
| 2008/0237040 A1 | 10/2008 | Wessel |
| 2008/0254544 A1 | 10/2008 | Modzelewski et al. |
| 2008/0275365 A1 | 11/2008 | Guthrie et al. |
| 2010/0267049 A1* | 10/2010 | Rutter ................ G01N 21/6428 |
| | | 435/7.1 |
| 2011/0042211 A1 | 2/2011 | Huang et al. |
| 2011/0111522 A1 | 5/2011 | Zimmerie et al. |
| 2013/0220839 A1 | 8/2013 | Chang et al. |
| 2014/0246334 A1 | 9/2014 | Bosch et al. |
| 2014/0262828 A1 | 9/2014 | Iyengar et al. |
| 2014/0349303 A1 | 11/2014 | Jennings |
| 2015/0276613 A1 | 10/2015 | Markovsky |
| 2017/0262663 A1 | 9/2017 | Davies |
| 2018/0150655 A1 | 5/2018 | Davies |

* cited by examiner

SYSTEMS AND METHODS FOR CORRECTION OF ON-STRIP CODING

RELATED APPLICATIONS

This application is a continuation patent application of U.S. application Ser. No. 15/879,699, filed Jan. 25, 2018, which is a divisional patent application of U.S. application Ser. No. 15/455,385 filed, Mar. 10, 2017, which claims the benefit of and priority to U.S. Provisional Application Ser. No. 62/306,927, filed, Mar. 11, 2016, the entirety of each of which are hereby incorporated herein by reference.

FIELD

The present disclosure relates to systems and methods for sensing a concentration of a constituent within a fluid through the use of diagnostic test strips.

BACKGROUND

Many individuals and industries have a need to monitor the concentration of particular constituents in a fluid. The oil refining industry, wineries, and the dairy industry are examples of industries where fluid testing is routine. In the health care field, individuals such as diabetics, for example, have a need to monitor a particular constituent within their bodily fluids. A number of systems are available that allow people to test a body fluid, such as, blood, urine, or saliva, to conveniently monitor the level of a particular fluid analyte, such as, for example, cholesterol, proteins, or glucose. Such systems can include a test strip where the user applies a fluid sample and a meter that "reads" the test strip to determine the analyte level in the fluid sample.

Further, accurate measurements of concentration levels in a body fluid, such as blood, may be critical to the long-term health of many users. As a result, there is a need for a high level of reliability in the meters and test strips used to measure concentration levels in fluids.

It would be advantageous to have a system which would allow for a cost effective auto-calibration system for diagnostic test strips that more reliably and more accurately provide a signaling code for individual test strips.

SUMMARY

The present disclosure is directed to systems, methods and devices for correction of coding on test strips.

In some embodiments, a method of making a diagnostic test strip comprises marking a machine-readable pattern onto the diagnostic test strip which contains information that allows a meter designed to work with the test strip to convert raw signal data from the diagnostic test strip into a meaningful concentration value for an analyte of interest; printing the machine-readable pattern having a modified based code that is different from a base code of the diagnostic test strip being produced, wherein the modified based code is based on a strip geometry parameter, a chemistry parameter or both the strip geometry and the chemistry parameters that are measured for the diagnostic test strip.

In some embodiments, a method of making a diagnostic test strip comprises obtaining a base code for a lot of test strips by testing a representative number of strips by destructive means; inspecting sub-lots of the lot of test strips by non-destructive means to determine variations in one or more parameters; and modifying the base code based on the variations in the one or more parameters.

These and other aspects and embodiments will be apparent to those of ordinary skill in the art by reference to the following detailed description and the accompanying drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

Figure 1A:
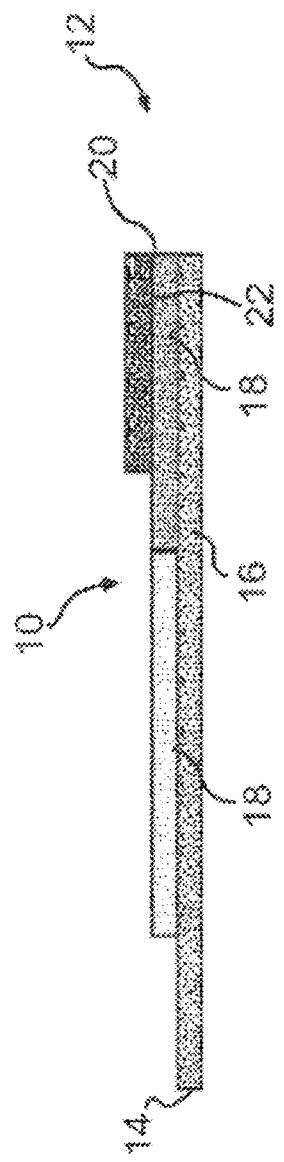
FIG. 1A is a general cross-sectional view of a test strip according to some embodiments of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods for measuring a body fluid constituent that includes a test strip and a meter. An individual test strip may also include an embedded code relating to data associated with a lot of test strips, or data particular to that individual strip. The embedded information presents data readable by the meter signaling the meter's microprocessor to access and utilize a specific set of stored calibration parameters particular to test strips, either based on characteristics of the manufacturing lot which includes the individual strip, or to an individual test strip.

According to aspects of the present disclosure, it is possible to use predetermined measured process parameters, such as geometry and/or chemistry parameters, that can be determined prior to the application of embedding the code on the individual test strip, so as to adjust or modify the embedded code to compensate for the variations in these parameters. This is distinct from the current industry standard practice of measuring the response of the assembled test strip using blood or contrived artificial samples. The current practice uses a destructive test on a sampling of the entire lot and provides an average code for the entire lot. With the inventive method, it is possible, in some embodiments, to measure every single test strip or a representative number of test strips produced within a lot non-destructively and offset an average lot code for individual portions of the lot.

This adjustment of the embedded code could be done for an entire test strip lot, or within a test strip lot for a group of test strips, as well as at an individual test strip level. For example, particular sub-lots of a test strip lot can read identical glucose solutions as either higher or lower than the test strip lot average for the same sample test strip lot. Sub-lot can refer to any arbitrary subset of an entire lot. For example, a lot may be made up of 50000 individual vials, each of which has 50 individual strips inside. A sub-lot could refer, for example, to the first 1000 vials of the lot, the first strip within each vial, or some other arbitrary grouping, even down to an individual strip. By determining how a particular parameter or parameters affects a test reading from the sample test strip lot, it is possible to adjust or modify the test readings based on this information by measuring a representative sample of the sensor produced within a lot non-destructively and offsetting the average lot code for individual portions of the lot. In some embodiment it is possible to convey the identified variations in these parameters; either prior to the time the individual test strip is embedded with a code or at a later time using the meter to modify the original embedded code to a new embedded code. The new embedded code may be physically embedded along with the original embedded code on the test strip, and/or the meter may contain data specific to identified variations in these parameters that is used with the original embedded code.

By way of a non-limiting example, variations in geometry parameters that may require an adjustment may include, but are not limited to, electrode size (width) or shape, distance between the electrodes, material from which the electrodes are produced, sample well height, sample well length, or aspect ratio of height versus electrode area. By way of a non-limiting example, variations in chemistry parameters that may require an adjustment may include, but are not limited to, type of enzyme, concentration of enzyme, concentration of mediator, ratio in concentrations of enzyme to mediator, electrolyte concentration, binder or other thickener concentration, crystal shape or orientation, and chemistry layer thickness. For example, as the reagent dries into a crystal form due to the ionic solids in the reagent from the electrolytes and the mediators, the size and shape of the crystals can vary based on a variety of factors, including but not limited to drying temperature and humidity.

Some aspects of the present disclosure provide improved techniques in conveying this information regarding these geometry and/or chemistry variations to the aforementioned test strip lots and/or meter, e.g. glucose meter, so as to correct the particular test strip lot code, among other things. The modified embedded coding identified for the individual test strips of the present disclosure may mitigate, among other things embedded coding errors or variations in a test strip lot due to particular parts of a test strip lot that can read higher or lower than the lot average for the same sample test strip lot; and may minimize the effect of normal process variations on biosensor readings, e.g., glucose biosensor readings. Furthermore, aspects of the present disclosure provide for improved technique(s) in conveying the geometry and/or chemistry variation information to the test strip lots and/or meter, to effectively increase the precision, and the quality, of test strip lots and diagnostics biosensors, e.g., meters. Further, by minimizing the effects of normal process variations on glucose biosensor readings, aspects of the present disclosure can result in a product that will perform more accurately in clinical settings, home settings, or the like.

FIG. 1A illustrates a general cross-sectional view of an embodiment of a test strip 10. Test strip 10 includes a proximal end 12, a distal end 14, and is formed with a base layer 16 extending along the entire length of test strip 10. The base layer 16 is preferably composed of an electrically insulating material and has a thickness sufficient to provide structural support to test strip 10. For purposes of this disclosure, "distal" refers to the portion of a test strip further from the fluid source (e.g., closer to the meter) during normal use, and "proximal" refers to the portion closer to the fluid source (e.g., a fingertip with a drop of blood for a glucose test strip) during normal use. The base layer 16 may be composed of an electrically insulating material and has a thickness sufficient to provide structural support to test strip 10.

As seen in FIG. 1A, the proximal end 12 of test strip 10 includes a sample receiving location, such as a sample chamber 20 configured to receive a patient's fluid sample, as described above. The sample chamber 20 may be formed in part through a slot in a dielectric insulating layer 18 formed between a cover 22 and the underlying measuring electrodes formed on the base layer 16. Accordingly, the sample chamber 20 may include a first opening, e.g., a sample receiving location, in the proximal end of the test strip and a second opening for venting the sample chamber 20. The sample chamber 20 may be dimensioned so as to be able to draw the blood sample in through the first opening, and to hold the blood sample in the sample chamber 20, by capillary action. The test strip 10 can include a tapered section that is narrowest at the proximal end 12, or can include other indicia in order to make it easier for the user to locate the first opening and apply the blood sample.

Figure 1B:
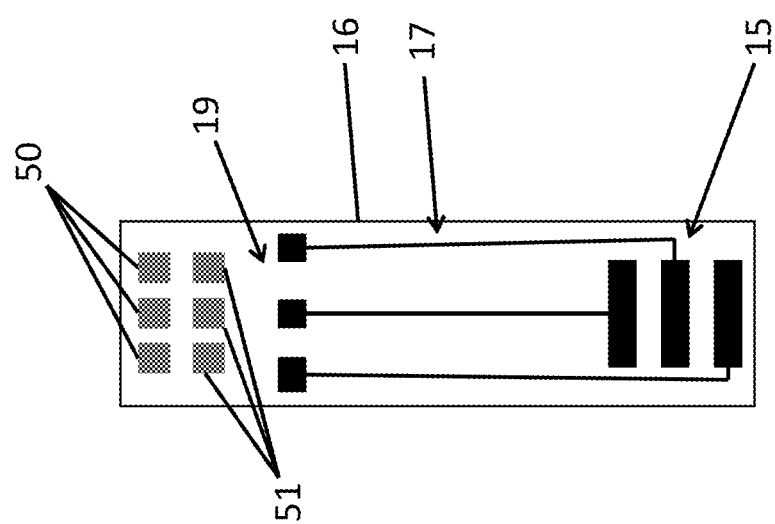
FIG. 1B is a is a top view of a conductive pattern on a substrate of a test strip according to some embodiments of the present disclosure.

In reference to FIG. 1B, disposed on base layer 16 is a conductive pattern. In some embodiments, the conductive pattern may be formed by laser ablating the electrically insulating material of the base layer 16 to expose the electrically conductive material underneath. Other methods may also be used, such as inserted conductors with physical attachment to control circuit. Other methods may also be used to dispose the conductive pattern on the base layer. The conductive pattern may include a plurality of electrodes 15 disposed on base layer 16 near proximal end 12, a plurality of electrical strip contacts 19 disposed on base layer 16 near distal end 14, and a plurality of conductive traces 17 electrically connecting the electrodes 15 to the plurality of electrical strip contacts 19.

A reagent layer may be disposed on the base layer 16 in contact with at least a working electrode of the conductive pattern. The reagent layer may include an enzyme, such as glucose oxidase, and a mediator, such as potassium ferricyanide or ruthenium hexamine. Reagent layer 90 may also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485). With these chemical constituents, the reagent layer reacts with glucose in the blood sample in the following way. The glucose oxidase initiates a reaction that oxidizes the glucose to gluconic acid and reduces the ferricyanide to ferrocyanide. When an appropriate voltage is applied to working electrode, relative to counter electrode, the ferrocyanide is oxidized to ferricyanide, thereby generating a current that is related to the glucose concentration in the blood sample.

By non-limiting example, it is possible a working electrode and counter electrode can be disposed in the sample chamber 20 optionally along with fill-detect electrodes. The reagent layer is disposed in the sample chamber 20 and preferably contacts at least the working electrode. The reagent layer, as explained above, may include an enzyme, such as glucose oxidase or glucose dehydrogenase, and a mediator, such as potassium ferricyanide or ruthenium hexamine. The test strip 10 has, near its distal end 14, a first plurality of electrical strip contacts that are electrically connected to the electrodes via conductive traces.

In some embodiments, a calibration code can be included on the test strip. In some embodiments, the calibration code can be included on the test strip in the form of a second plurality of electrical strip contacts near the distal end of the strip. The second plurality of electrical contacts can be arranged such that they provide, when the strip is inserted into the meter, a distinctly discernable calibration code specific to the test strip lot readable by the meter. As noted above, the readable code can be read as a signal to access data, such as calibration coefficients, from an on-board memory unit in the meter related to test strips from that lot, or even information corresponding to individual test strips. For example, as shown in FIG. 1B, the test strip can include a calibration code in the form of a plurality contacts 50. In some embodiments, more than one calibration code can be included on the test strip. For example, the test strip can include a second calibration code in the form of a second plurality of contacts 51, as shown in FIG. 1B.

Figure 2A:
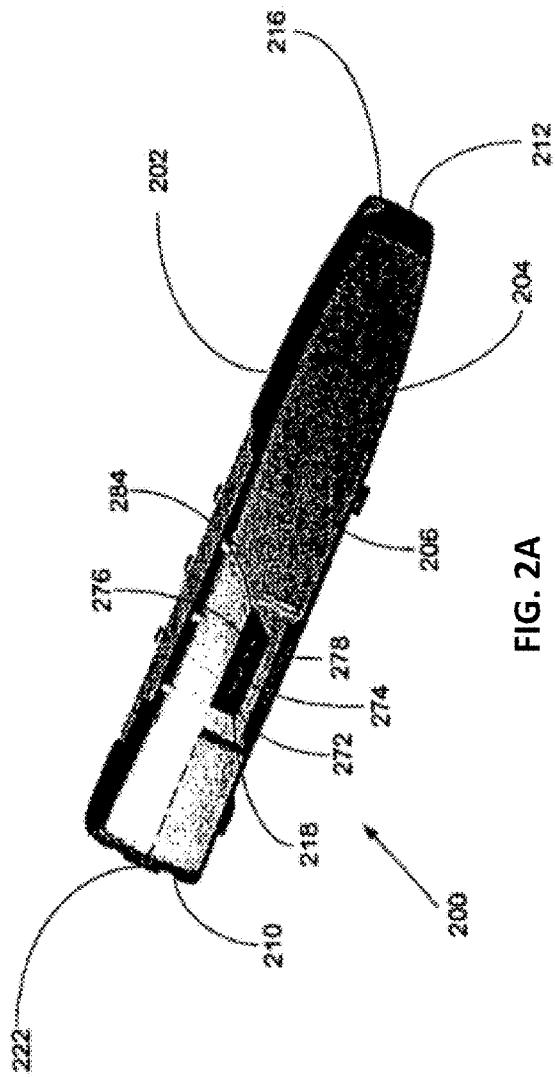
FIG. 2A is a perspective view of a meter, according to some embodiments of the present disclosure.
Figure 2B:
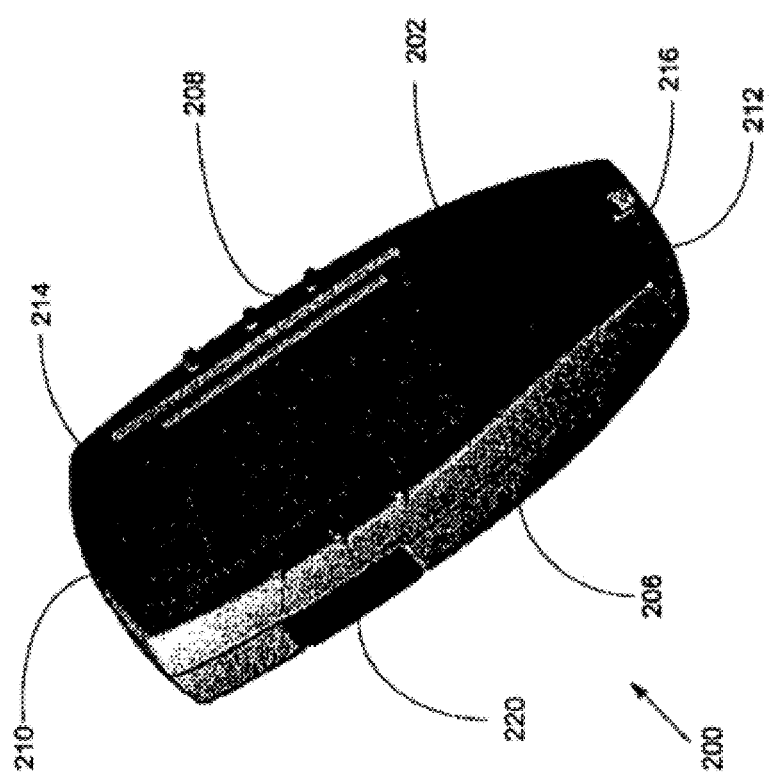
FIG. 2B is a perspective view of the meter of FIG. 10, with a removable data storage device inserted in it, according to some embodiments of the present disclosure.

FIG. 2A and FIG. 2B illustrates a meter 200 used to measure the glucose level in a blood sample. In some embodiments, the meter 200 has a size and shape to allow it to be conveniently held in a user's hand while the user is performing the glucose measurement. Meter 200 may include a front side 202, a back side 204, a left side 206, a right side 208, a top side 210, and a bottom side 212. The front side 202 may include a display 214, such as a liquid crystal display (LCD). A bottom side 212 may include a strip connector 216 into which test strip can be inserted to conduct a measurement. The top side 210 may include one or more user controls 222, such as buttons, with which the user may control meter 200, and the right side 208 may include a serial connector (not shown).

Referring to FIG. 2A and FIG. 2B, the meter 200 may use data from a removable data storage device or from internal memory to calculate glucose levels in blood samples measured by meter 200. Specifically, such data may be associated with a lot of test strips and may store one or more parameters that meter 200 may use for that lot. For example, the data may include one or more calibration parameters that meter 200 may use to calculate the glucose level from an averaged current measurement. The calibration parameters may include temperature corrections, hematocrit corrections, or other corrections. Data may further include other information related to the lot of test strips and the meter, such as a code identifying the brand of test strips, a code identifying the model of meter to be used, and an expiration date for the lot of test strips.

The test strip may include a code which contains information that allows a meter designed to work with the test strip to convert the raw signal from the test strip into a meaningful concentration value for an analyte of interest. An example of encoding a strip with a lot code would be a simple binary bit system which could be read electrically by the meter. This binary code could be associated with a lookup table inside the meter. By way of a non-limiting example, some methods for encoding test strips are disclosed in a commonly owned U.S. Pat. No. 9,012,232, which is incorporated herein by reference in its entirety. Other methods to code the test strips may also be employed.

In some embodiments, the original base code(s) relates to data associated with a specific lot of test strips. A typical current industry practice is measuring the response of the assembled test strip using blood or contrived artificial samples. The current practice uses a destructive test on a sampling of the entire lot and provides an average code for the entire lot. This can be referred to as the base code of the lot. However, the base code is not necessarily generated this way. Some manufacturers use a 'universal code', where every lot has the same base code. This is typically done when the process is stable enough or the performance requirements are wide enough that individual lot coding is not necessary. The embedded information from the test strip presents data readable by the meter that may be used to signal the meter's microprocessor to access and utilize a specific set of stored calibration parameters particular to test strips from a manufacturing lot to which the individual strip belongs, or to an individual test strip. However, exact process parameters may vary among the test strips in the lot, and thus sub-lots may be further tested by non-destructive means to obtain a code that is more specific for each sub-lot. A sub-lot may be any subset of the entire amount of test strips from the lot, from an arbitrary percentage down to a single test strip.

According to some aspects of the present disclosure, the original identified base code(s) can be modified prior to embedding the code on the test strip at the time of manufacturing to compensate for variations in parameters, such as, predetermined measured process parameters, e.g., geometry and/or chemistry parameters, which can be detected by non-destructive means so the test strips can still be provided to users. Codes are an important part of designing accurate biosensors. The following is a step by step process of how they operate:

1. A test strip lot is made on the manufacturing line up to a certain point of development. At this point, the strips are functional in that they produce results on a meter, but they are uncoded so the results as displayed may be inaccurate.
2. A portion of the test strip lot is sampled. These test strip samples are tested using natural or artificial specimens containing the analyte of interest (e.g., blood would be an example of a natural specimen, a control solution containing the analyte of interest would be an example of an artificial specimen). Specimens having a variety of analyte levels are tested. After the tests, the test strips used in the tests are discarded as they cannot be used again for testing.
3. A dose response of analyte level in the specimen versus signal generated (e.g. absorbance or current) is constructed and an equation created that describes the relationship. The equation may be in the form y=ax+b or $y=ax^2+bx+c$, where x is the signal and y is the analyte value. It should be noted that the base code may be generated by other means.
4. At this step, the path forward is determined by the coding method used in the system. Proceeding on the example above, which uses a binary system to reference a lookup table containing coefficients within the meter, the dose response obtained in step 3 is compared to the available coefficient sets in the meter. The coefficient set that provides the best performance is selected. In other embodiments, other coding systems, including but not limited to a logical system (for example, XOR, OR, AND), can be used.
5. The selected code is then marked onto the test strips for this lot. When a test strip from this lot is inserted into a meter, the lot code will be read by the meter and a lookup table will be accessed. The meter will then use the coefficients provided in the lookup table to convert signal into a meaningful analyte concentration. This will be the displayed result on the meter (however, additional transformations, for example, temperature compensation, may be completed after the conversion but before the display, so the actual result displayed may vary).
6. However, as noted above, some portions or sub-lots of the entire lot, or each test strip in the lot, may be examined to detect process parameters, e.g., geometry and/or chemistry parameters, among other variations. Such variations may be determined with non-destructive means, so that the test strip can still be used for future tests. Based on the observed variations in the parameters, the base code may be adjusted so that the meter uses different parameters for different sub-lots or test strips in the lot, thus resulting in a more accurate test result for each test strip.

By way of example, particular parts of a test strip lot can read higher or lower than the test strip lot average for the same sample test strip lot. By determining how a particular parameter or parameters affects an original test reading, from the sample test strip lot, it is possible to adjust or modify the test readings based on this information before embedding the test strip lot with a code. For example, a diagnostic test strip may have a code put directly on the test strip by means of conductive patterns. This pattern is applied directly to the test strip at the time of manufacture. If the geometry and/or chemistry parameters are known prior to the application of this code, it is possible, for example, by means of an algorithmic system, to adjust the code to compensate for the variations in these parameters. This adjustment can be done for an entire lot, or within a lot, even down to the individual test strip level. For example, if a test strip had an anode size 2% larger than the test strip lot mean, and this caused code 128 to be optimal instead of code 112, code 128 would be printed onto the test strip by the manufacturing equipment.

In some embodiments of the present disclosure, after the individual test strip is embedded with the original identified base code, a second code may be embedded on the same individual test strip at some earlier or later time. The second code may include a modification of the original identified base code with the predetermined measured process parameters data, e.g., identified variations in geometry and/or chemistry parameters. The following is a non-limiting example of how to achieve this modification:

1. Establish a base code as described above (the order of this step may not be critical, depending on particulars of the process, it can be done before or after the secondary code is added).
2. A physical measurement is done on the test strip. In this example, it will be supposed that the measurement is done on every individual test strip.
3. Using an algorithm, an offset is calculated based on the mean of the physical measurements of the entire lot versus the physical measurement of the individual test strip in question. For example, if the electrode area of the sensor in question is 4% larger than the mean lot size, a −4% offset could be calculated to bring that sensor's projected signal in line with the average for the entire lot. Any mathematical transformation could be accomplished by the second code. For example, instead of a fixed offset, a quadratic equation based on temperature might be used. The modification of the first code may be directly encoded (as in, a value of 4 encoded on the strip translates into a +4 offset), or it may reside in a lookup table on the meter (where a value of 4 would cause the meter to look for the matching coefficients in a lookup table residing in the meter's memory). Other methods of encoding may also be used.
4. A marking indicating this offset will be made on this individual test strip, where the marking is different than the marking indicating the base code. This marking may use a binary or arbitrary base system (trinary, etc.) and may be referenceable to a lookup table in the meter or may represent a direct translation, where the marking on the strip is used to perform an operation to the code or the result using this coefficient. For instance, a marking indicating the binary value 0-100 may indicate −4%, or an arbitrary value that references a lookup table entry, for example 0110110 may be used.
5. The meter will use the −4% offset to directly adjust the given value. For instance, if the reading obtained by the meter were 200 mg/dL glucose, this may be offset to 192 mg/dL as a final reading that is reported by the device.

By way of example, the method of adding at least one additional coding, e.g., a second embedded coding, to the test strip, can be used regardless of how or where test strip lot information is encoded. In particular, the method could use an offset encoded onto the test strip. For example, if a test strip had an anode size 2% larger than the test strip lot mean, the test strip could be coded with a −2% offset to cancel out the effect of the larger anode. This offset could, for example, be transcribed directly as a binary code, or be transcribed as a code that could then be interpreted via a lookup table in the meter. It is noted that these exemplary methods are not intended to be limiting to this embodiment of the present disclosure. The offset may be a fixed amount, a percentage offset, or a non-fixed offset that is encoded in a lookup table on the meter.

The presently disclosed systems and methods provide many advantages, by non-limiting examples: a) it may provide for an economical solution to improving the quality and precision of the test strip and/or meter for both manufacturing of the test strip and utilizing the meter; and b) it can deliver a product to consumers that performs more accurately in clinical settings or home settings.

By way of a non-limiting example, FIGS. 3-6 show the dependence between geometry parameters and glucose readings.

Figure 3:
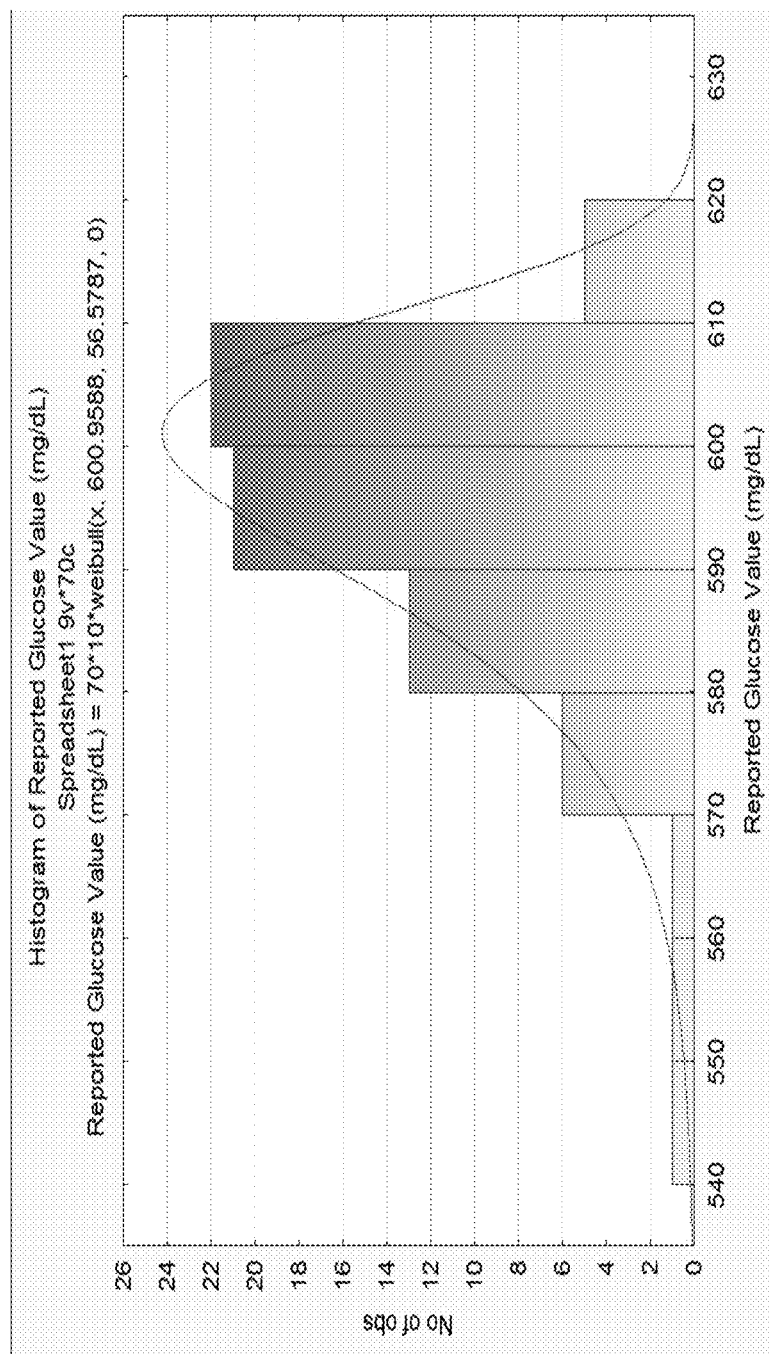
FIG. 3 is a histogram showing reported glucose results from a group of biosensors with all the biosensors in the group using the same code to translate signal into a glucose value, according to some embodiments of the present disclosure.

FIG. 3 is a histogram showing reported glucose results from a group of biosensors with all the biosensors in the group using the same code to translate signal into a glucose value. For example, in FIG. 3, the mean of the data set using a particular sample is approximately 601 mg/dL, and the standard deviation is 13.6. The data points are also non-normally distributed. If it is known how a particular parameter or parameters affects a sample reading, then, it is possible to adjust readings based on this information. First, the original/same code is taken in a step by step definition, as described above; and then the geometry parameter is combined (mathematical formula) with the original glucose reading for FIG. 3, as described below.

Figure 4:
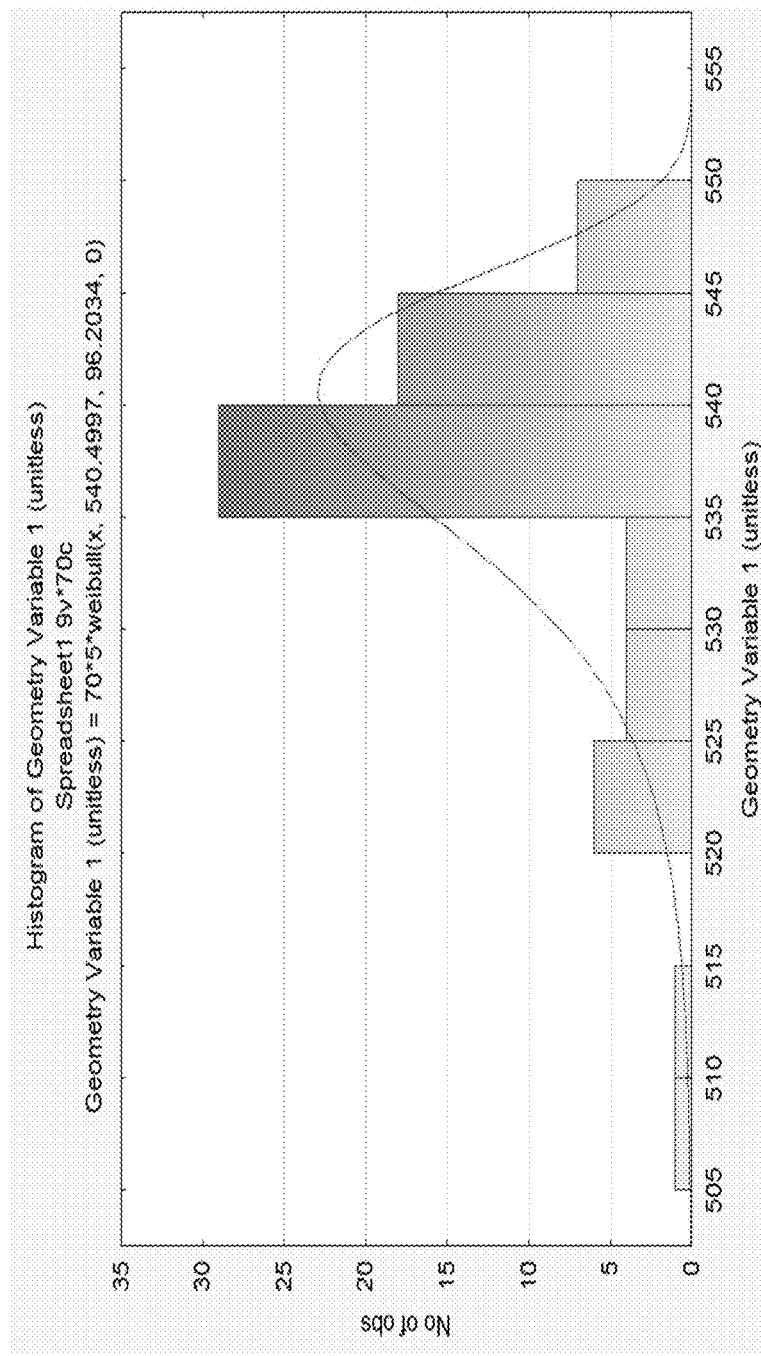
FIG. 4 is a histogram showing a geometry parameter measured on the same biosensors of FIG. 3, according to some embodiments of the present disclosure.
Figure 5:
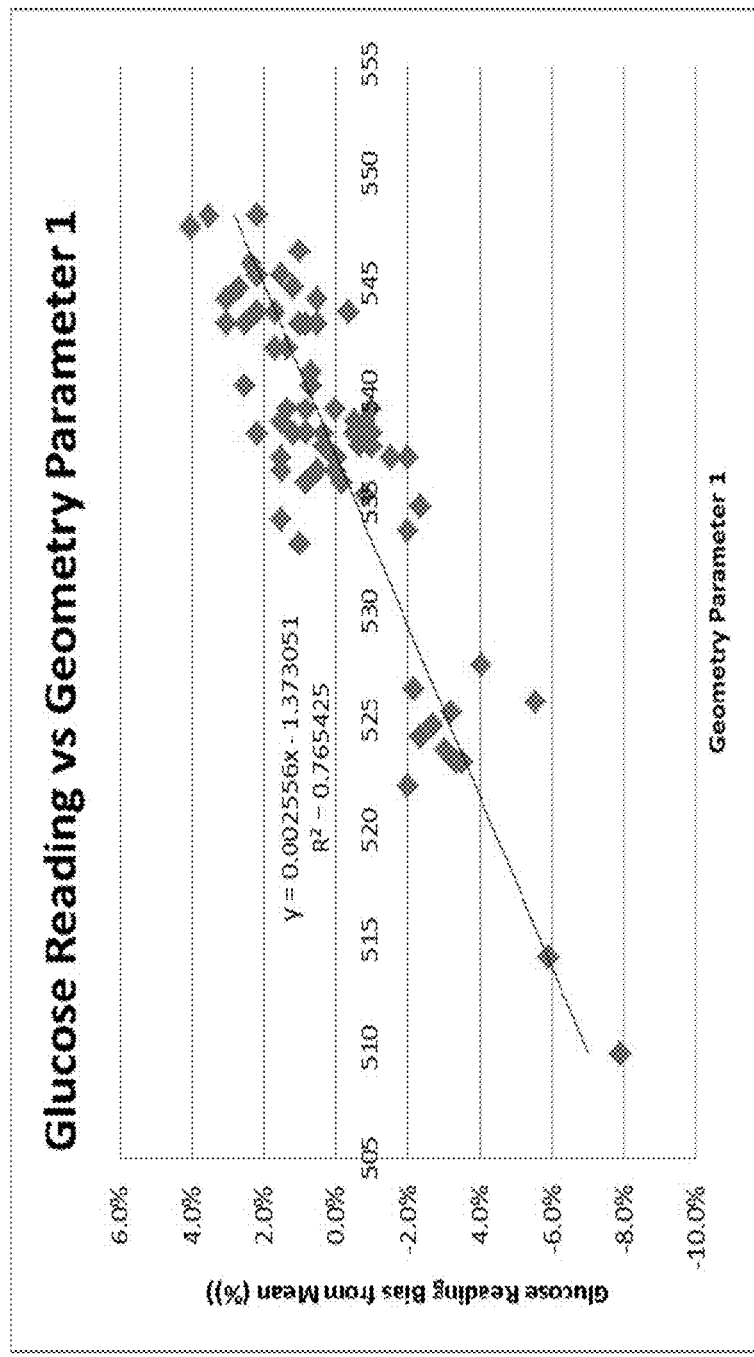
FIG. 5 is a scatter plot of FIG. 4 showing each test strip's geometry parameter versus the bias from the mean of the glucose reading obtained, according to some embodiments of the present disclosure.

FIG. 4 shows a geometry parameter measured on the samples from FIG. 3. In particular, it is possible to relate bias from the mean of the readings to the geometry parameter, as shown in FIG. 5. In this particular example, the geometry parameter is related to the glucose reading bias through a linear equation of the form y=ax+b. In this particular equation every 10 units of the geometry parameter affects the glucose reading by about 2.5%. However, other types of relationships are possible. FIG. 5 is a scatter plot of FIG. 4 showing each test strip's geometry parameter versus the bias from the mean of the glucose reading obtained.

Figure 6:
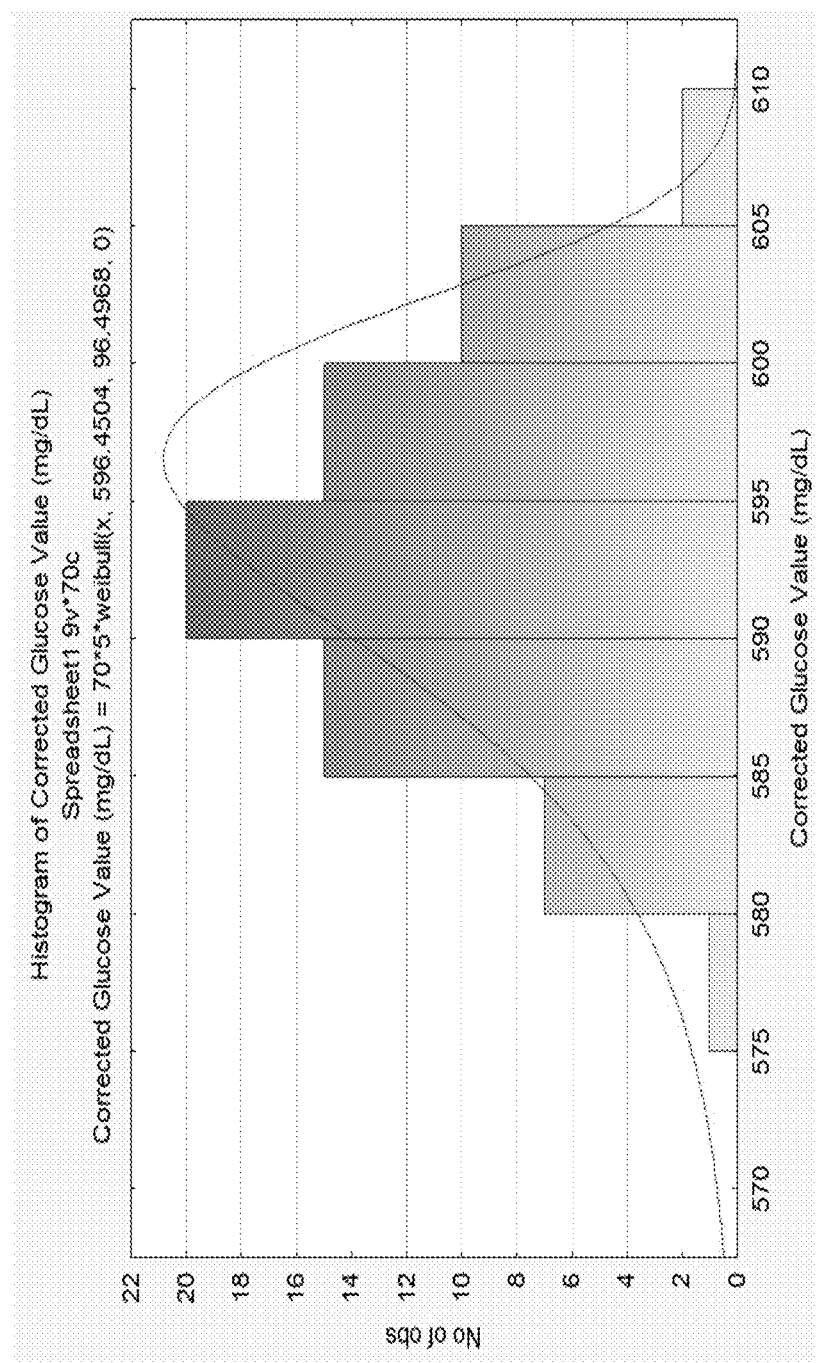
FIG. 6 is a histogram showing the corrected glucose results from FIG. 4 according to some embodiments of the present disclosure.

FIG. 6 shows the corrected glucose reading as a result of applying the geometry parameter correction equation (shown in FIG. 5) to the original glucose readings. For example, if the mean of the lot has a geometry parameter of approximately 537, and the sub-lot in question has a measurement of 527, a +2.5% offset will be applied in order to adjust the readings upward. The standard deviation of the corrected glucose readings is 6.6, a statistically significant improvement compared to the original readings' standard deviation of 13.6. Correcting for this geometry parameter alone removed approximately 75% of the variance from this data set (185 versus 43.5 where variance is the square of the standard deviation).

Figure 7:
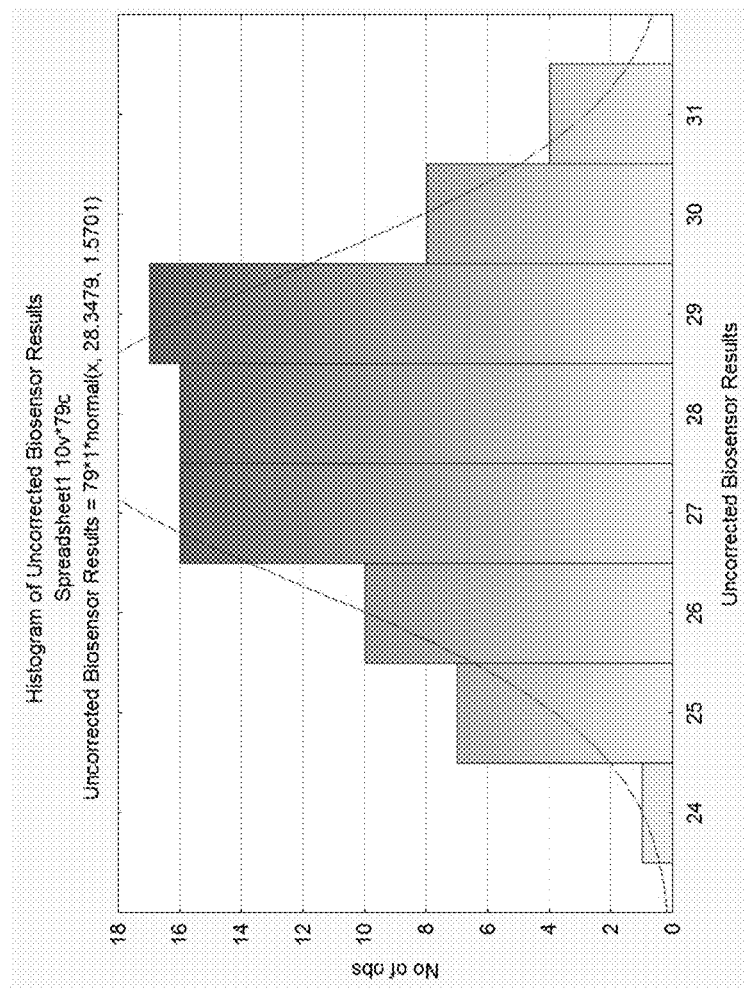
FIG. 7 is a histogram showing a chemistry parameter measured on the same biosensors of FIG. 3, according to some embodiments of the present disclosure.
Figure 8:
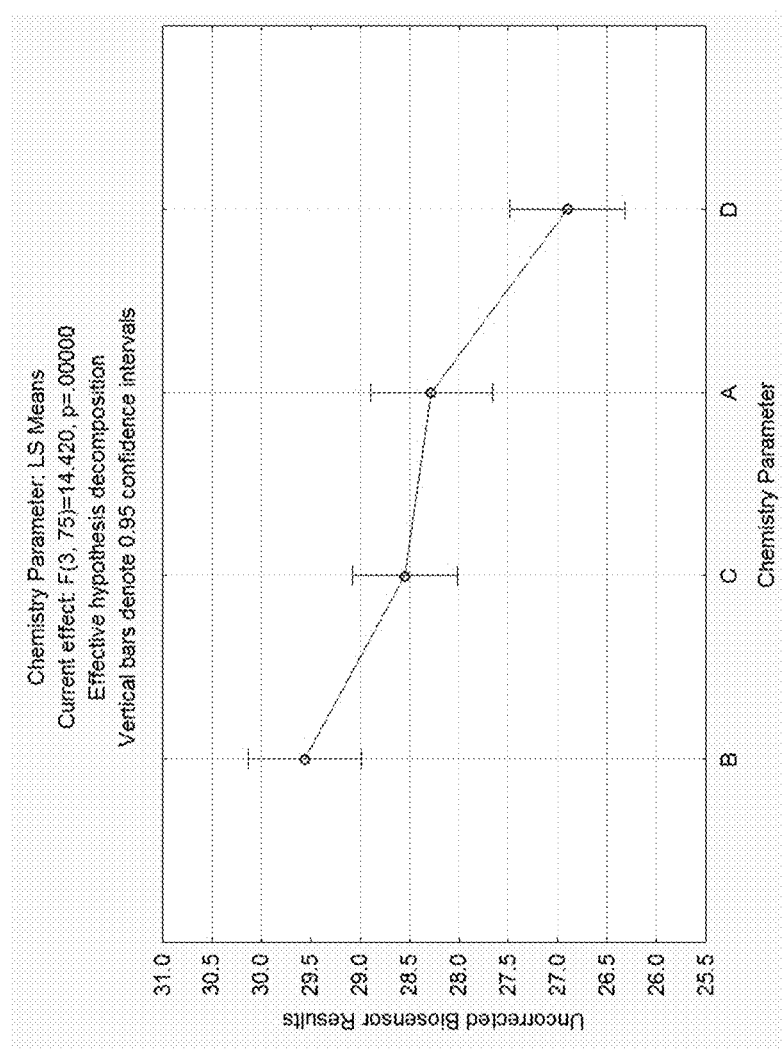
FIG. 8 is a plot of data in FIG. 7, showing each test strip's chemistry parameter versus the bias from the mean of the glucose reading obtained, according to some embodiments of the present disclosure.
Figure 9:
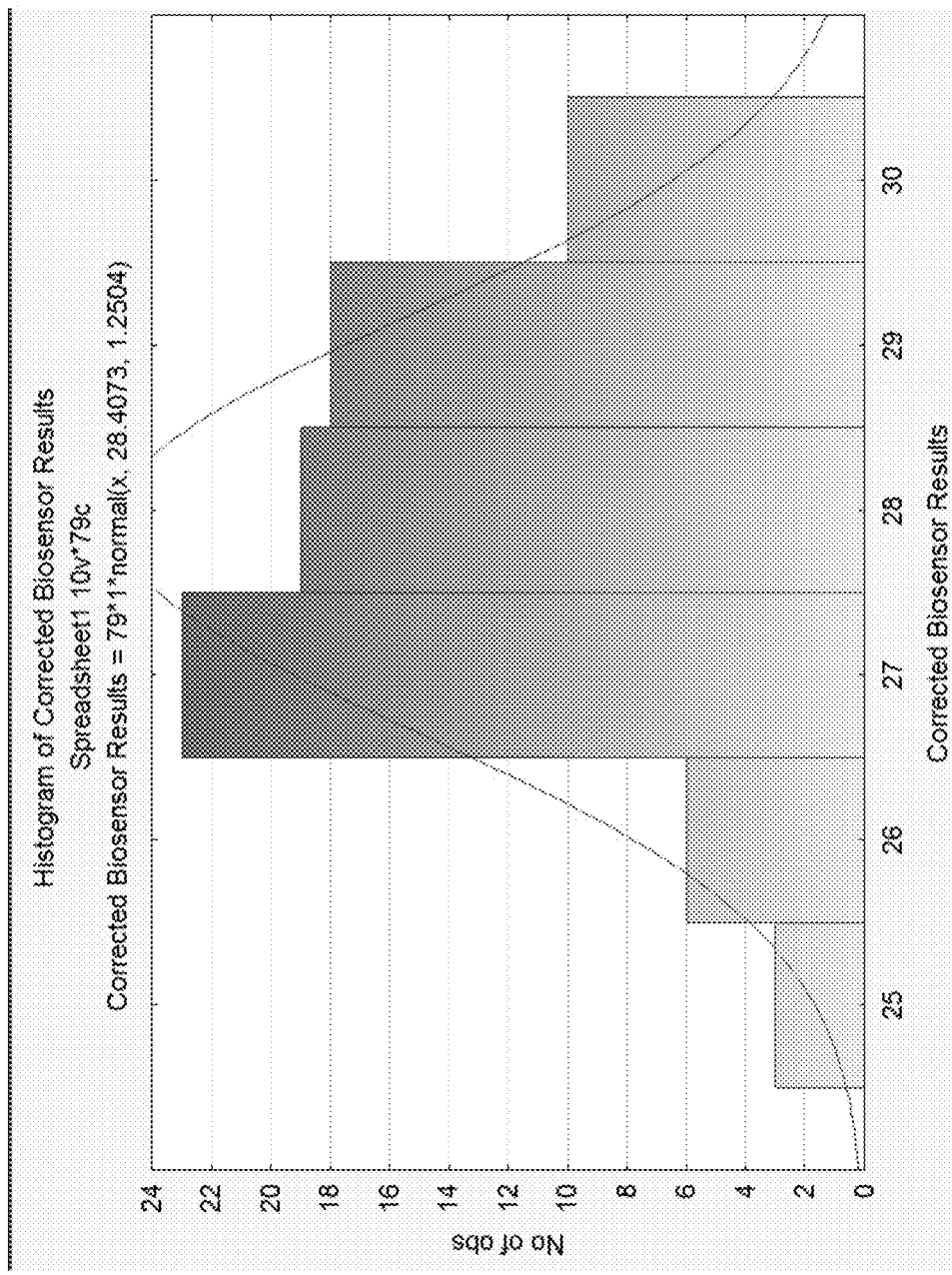
FIG. 9 is a histogram showing the corrected glucose results of FIG. 7, according to some embodiments of the present disclosure.

By way of a non-limiting example, FIGS. 3-6 show the dependence between chemistry parameters and test readings (in this case, hematocrit). Although previous examples have used a linear equation to correct for a variable, non-linear correlations can also be used. For example, the uncorrected data set in FIG. 7 shows a standard deviation of approximately 1.57. By observing the factors involved in the scheme, a one-way ANOVA analysis can be performed to determine how each category of the chemistry factor affects readings, which is shown in FIG. 8. FIG. 9 shows the corrected variable, with a standard deviation of 1.25.

According to aspects of the present disclosure, improved technique(s) in conveying the geometry and/or chemistry variation information to the test strip lots and/or the meter can effectively increase the precision, and the quality, of test strip lots and diagnostics biosensors, e.g. meters, among other things.

According to aspects of the present disclosure, embodiments of the present disclosure includes a test strip, a method of determining a constituent level within a fluid, a method of making a test strip, and a method of making a plurality of test strips that obviate one or more of the limitations and disadvantages of prior devices and methods.

In some embodiments, the present disclosure is directed to a diagnostic test strip or sensor. Encoded on the test strip is a machine-readable marking which contains information that allows a meter designed to work with the test strip to convert the raw signal from the diagnostic test strip into a meaningful concentration value for an analyte of interest. The machine-readable marking that is encoded on a particular test strip is selected at the time of printing and may vary from the base code of a particular test strip lot based on strip geometry or chemistry parameters that are measured for each sub-lot grouping. A sub-lot may be any subset of the entire amount of test strips from the lot, from an arbitrary percentage down to a single test strip.

In some embodiments, the present disclosure is directed to a diagnostic test strip or sensor. Encoded on the test strip is a machine-readable marking which contains information that allows a meter designed to work with the test strip to convert the raw signal from the diagnostic test strip into a meaningful concentration value for an analyte of interest. Also encoded is a second machine-readable marking that instructs the meter to offset the base code by a particular amount based on the cipher contained in the second machine-readable marking. The second machine-readable marking that is encoded on a particular test strip is selected based on strip geometry or chemistry parameters that are measured for each sub-lot grouping. A sub-lot may be any subset of the entire amount of test strips from the lot, from an arbitrary percentage down to a single test strip.

In some embodiments, the present disclosure provides for a method of making a diagnostic test strip, said method comprising: marking a machine-readable pattern onto the test strip which contains information that allows a meter designed to work with the test strip to convert the raw signal from the diagnostic test strip into a meaningful concentration value for an analyte of interest. The pattern printed being chosen at the time of printing and possibly varying from the base code of the particular test strip lot being produced based on strip geometry or chemistry parameters that are measured for each sub-lot grouping.

In some embodiments, the present disclosure provides for method of making a diagnostic test strip, said method comprising: marking a machine-readable pattern onto the test strip which contains information that allows a meter designed to work with the test strip to convert the raw signal from the diagnostic test strip into a meaningful concentration value for an analyte of interest. Additionally marking a second machine-readable pattern onto the test strip which instructs the meter to offset the base code of the first pattern by a certain amount, where the second pattern is chosen based on strip geometry or chemistry parameters that are measured for each sub-lot grouping.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A diagnostic test strip comprising:
a base code comprising information that allows a meter designed to work with a plurality of diagnostic test strips to convert raw signal data from one or more electrodes on the plurality of diagnostic test strips into a meaningful concentration value for an analyte of interest; and
a modified code being different from the base code of the plurality of diagnostic test strips,
wherein the modified code modifies information encoded by the base code based on a difference in an average value for the plurality of diagnostic test strips of one or more strip geometry parameters, one or more chemistry parameters, or both the one or more strip geometry parameters and the one or more chemistry parameters and a corresponding value for the diagnostic test strip.

2. The test strip of claim 1, wherein the modified code refers to a lookup table of the meter such that the concentration value of the analyte of interest can be modified based on the modified code.

3. The test strip of claim 1, wherein the meter is a glucose meter and the analyte is blood glucose.

4. The test strip of claim 1, wherein the modified code onto the test strip instructs the meter to offset the base code by a certain amount.

5. The test strip of claim 1, wherein the one or more geometry parameters include one or more of an electrode width of the electrode on the test strip, a distance between electrodes on the test strip, electrode material, a sample well height, and a sample well length.

6. The test strip of claim 1, wherein the one or more chemistry parameters includes one or more of type of enzyme, concentration of enzyme, concentration of a mediator, electrolyte concentration, and chemistry layer thickness.

7. A test strip formed by a method comprising:
marking a base code of a machine-readable pattern onto a diagnostic test strip from a plurality of diagnostic test strips, the base code comprising information that allows a meter designed to work with the plurality of diagnostic test strips to convert raw signal data from one or more electrodes on the plurality of diagnostic test strips into a meaningful concentration value for an analyte of interest;
marking a modified code of a machine-readable pattern onto the diagnostic test strip of the plurality of diagnostic test strips, the modified code being different from the base code of the plurality of diagnostic test strips being produced,
wherein the modified code modifies information encoded by the base code based on a difference in an average value for the plurality of diagnostic test strips of one or more strip geometry parameters, one or more chemistry parameters, or both the one or more strip geometry parameters and the one or more chemistry parameters and a corresponding value for the diagnostic test strip.

8. The test strip of claim 7, wherein the modified code refers to a lookup table of the meter such that the concentration value of the analyte of interest can be modified based on the modified code.

9. The test strip of claim 7, wherein the meter is a glucose meter and the analyte is blood glucose.

10. The test strip of claim 7, wherein the marking of the modified code onto the diagnostic test strip instructs the meter to offset the base code of the first machine-readable pattern by a certain amount.

11. The test strip of claim 7, wherein the one or more geometry parameters include one or more of an electrode width of the electrode on the test strip, a distance between electrodes on the test strip, electrode material, a sample well height, and a sample well length.

12. The test strip of claim 7, wherein the one or more chemistry parameters includes one or more of type of enzyme, concentration of enzyme, concentration of a mediator, electrolyte concentration, and chemistry layer thickness.

13. A diagnostic system comprising:
a plurality of diagnostic test strips; and
a meter designed to perform diagnostic tests using a plurality of diagnostic test strips,
wherein one or more of diagnostic test strips of the plurality of diagnostic test strips comprise:
a base code comprising information that allows the meter to convert raw signal data from one or more electrodes on the plurality of diagnostic test strips into a meaningful concentration value for an analyte of interest; and a modified code being different from the base code of the plurality of diagnostic test strips, wherein the modified code modifies information encoded by the base code based on a difference in an average value for the plurality of diagnostic test strips of one or more strip geometry parameters, one or more chemistry parameters, or both the one or more strip geometry parameters and the one or more chemistry parameters and a corresponding value for the one or more diagnostic test strips.

14. The diagnostic system of claim 13, wherein the modified code refers to a lookup table of the meter such that the concentration value of the analyte of interest can be modified based on the modified code.

15. The diagnostic system of claim 13, wherein the meter is a glucose meter and the analyte is blood glucose.

16. The diagnostic system of claim 13, wherein the modified code onto the test strip instructs the meter to offset the base code by a certain amount.

17. The diagnostic system of claim 13, wherein the one or more geometry parameters include one or more of an electrode width of the electrode on the test strip, a distance between electrodes on the test strip, electrode material, a sample well height, and a sample well length.

18. The diagnostic system of claim 13, wherein the one or more chemistry parameters includes one or more of type of enzyme, concentration of enzyme, concentration of a mediator, electrolyte concentration, and chemistry layer thickness.

* * * * *